Figure 1:
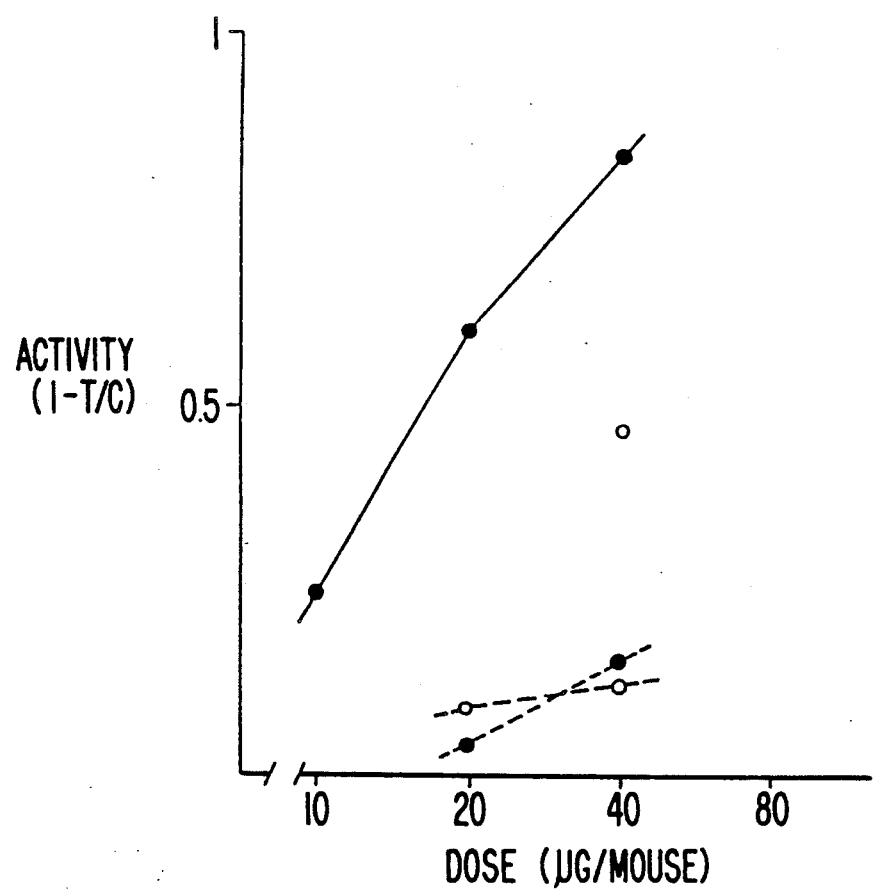

United States Patent [19]

Ogawa et al.

[11] Patent Number: 5,094,854

[45] Date of Patent: Mar. 10, 1992

[54] LIPOSOME COMPOSITION USEFUL FOR HYPERTHERIA THERAPY

[75] Inventors: Yasuaki Ogawa, Otokuni; Katsumi Iga, Suita; Yasutaka Igari, Kobe, all of Japan

[73] Assignee: Takeda Chemical Industries, Ltd., Osaka, Japan

[21] Appl. No.: 607,647

[22] Filed: Oct. 31, 1990

Related U.S. Application Data

[63] Continuation of Ser. No. 319,133, Mar. 6, 1989, abandoned.

[30] Foreign Application Priority Data

Mar. 4, 1988 [JP] Japan .................................. 63-52249

[51] Int. Cl.$^5$ ..................... A61K 9/133; A61K 9/127; B01J 13/02
[52] U.S. Cl. ..................... 424/423; 264/4.1; 264/4.6; 428/402.2; 424/450; 514/963
[58] Field of Search ......................... 428/402.2, 402.21; 424/450, 423; 264/4.6, 4.1, 4.3

[56] References Cited

U.S. PATENT DOCUMENTS

| | | | |
|---|---|---|---|
| 4,755,388 | 7/1988 | Heath et al. | 424/450 |
| 4,765,987 | 8/1988 | Bonte et al. | 424/450 |
| 4,844,904 | 7/1989 | Hamaguchi et al. | 428/402.2 X |

FOREIGN PATENT DOCUMENTS

072234  2/1983  European Pat. Off. .
0126580 11/1984 European Pat. Off. ............ 424/450

OTHER PUBLICATIONS

Gruner et al., 'Novel Multilayered Lipid Vesicles . . .', Biochemistry, vol. 24, (1985) pp. 2833-2842.
Yatvin et al., Science, vol. 202, 22 Dec. 1978, pp. 1290-1292.
Yatvin et al., Cancer Research, vol. 41, 1602-1607, May 1981.
Bassett et al., The Journal of Urology, vol. 135, 612-615 (1986).
Weinstein et al., Science, vol. 204, 13 Apr. 1979, pp. 188-191.
Magin et al., Chemical Abstracts 97:203147d (1982).
Ni et al., Chemical Abstracts 107:111441s (1987).
Yatvin et al., Chemical Abstracts 94:214521k (1981).
Lichtenberg et al., Biochemistry, vol. 20, 3462-3467 (1981).

Primary Examiner—Richard D. Lovering
Assistant Examiner—John M. Covert
Attorney, Agent, or Firm—Wenderoth, Lind & Ponack

[57] ABSTRACT

This invention relates to the liposome compositions which are characterized in that the phase transition temperature of the membrane is in the range of 40° to 45° C. and the osmotic pressure of a drug-containing solution to be entrapped in liposomes is 1.2 to 2.5 times higher than that of body fluid of warm-blooded animals. The compositions are useful for treatment of solid tumors in hyperthermia therapy.

18 Claims, 1 Drawing Sheet

LIPOSOME COMPOSITION USEFUL FOR HYPERTHERIA THERAPY

This application is a continuation of now abandoned application Ser. No. 07,319,133 filed on Mar. 6, 1989.

This invention relates to liposome compositions in which a drug is entrapped in liposomes and the methods for their production.

As a therapy for tumor, the hyperthermia therapy has been practiced very often lately, the therapy that the site of tumor is heated to a temperature higher than the normal body temperature by several degrees (to 40°–45° C.) so that only tumor cells may specifically be damaged. For the treatment of tumor the therapy is not adopted alone but combined with a chemotherapy in expectation of obtaining the full effect of the therapy (Jpn. J. Hyperthermic Oncol. 2, No. 3, 1986). On the other hand, chemotherapy has a problem that it may have severe side effects on normal cells so that choice of an adequate dose is difficult. The use of the so-called thermosensitive liposomes characterized by release of the entrapped drug at a temperature in the range of hyperthermia has recently been attempted so as to deliver the drug at a high level into cancer cells by administration of a relatively small dose, enhancing the targeting effect and hence the therapeutic effect. The reports on this include:

(1) Yatvin et al., Science, 202, 1290 (1978)
(2) Yatvin et al., Cancer Res., 41, 1602 (1981)
(3) Bassett et al., J. Urol., 135, 612 (1986).

The procedures described in these reports aim at causing the phase transition of the liposomal membrane by heating when the liposomes administered intravenously have been brought through the blood flow to the site of tumor, so that the drug entrapped in the liposomes may be released and distributed efficiently in its free form.

As described above, use of thermosensitive liposomes in hyperthermia therapy may be a promising targeting therapy for tumor. However such a targeting effect depends upon how stably the liposomes administered circulate through the circulatory system at the normal body temperature and how much the liposomes release the drug at the site of tumor at the temperature of hyperthermia. The thermosensitive liposomes reported so far have problems with respect to the stability and the release by heating, and may not be expected to show their full effect. For example, the liposomes described in Science, 202, 1290 (1978) release only a small amount of the drug at the temperature of hyperthermia, and the liposomes described in J. Urol., 135, 162 (1986) release a certain amount of the drug already at a temperature lower than that of hyperthermia (e.g. 37 39° C.). Thus the liposomes prepared by the conventional methods have problems to be solved with respect to release by heating and stability.

Namely, we have not had yet practically useful liposome compositions which have a membrane showing a phase transition at the temperature of hyperthermia (40°–45° C.), entrap a drug at a high concentration for a long time when kept at a temperature lower than that of hyperthermia, and release the drug efficiently in a very short time at the temperature of hyperthermia or higher.

Under the circumstances described above, the inventors have investigated the methods for efficient release of the drug entrapped in liposomes administered intravenously in the local tissues heated for hyperthermia therapy, by adjusting the osmotic pressure of the drug-containing solution to be entrapped in liposomes and choosing the construction of liposomes, and have completed this invention. Namely this invention relates to (1) liposome compositions in which a drug-containing solution of an osmotic pressure 1.2 to 2.5 times higher than that of body fluid of warm-blooded animals is entrapped in said liposomes, wherein the liposomes have a membrane with a phase transition temperature of 40°–45° C., (2) the compositions described in the above item (1) wherein the main component of the liposomal membrane is a phospholipid of which acyl groups are saturated acyl groups, (3) the compositions described in the above item (1) or (2) wherein the drug is an antitumor agent, (4) the drug described in the above item (1), (2), or (3) wherein the liposomes are large unilamellar vesicles, (5) a method for production of liposome compositions, characterized by formation of liposomes which entrap a drug-containing solution of an osmotic pressure 1.2 to 2.5 times higher than that of body fluid of warm-blooded animals and the phase transition temperature of which membrane is 40°–45° C., and (6) the method for production of liposome compositions described in the above item (5) wherein the liposomal membrane is formed by using a phospholipid of which acyl groups are saturated acyl groups as the main material.

The liposome compositions in this invention are prepared so that the liposomal membrane may show phase transition at the temperature of hyperthermia, i.e. so that the phase transition temperature of the membrane may be 40°–45° C., preferably 40°–43° C. As the material of this membrane, various phospholipids of which acyl groups are saturated acyl groups (hereinafter sometimes abbreviated to "saturated phospholipids") are used separately or in combination very advantageously. For example, glycerophospholipids are preferably used which have two acyl groups of the formula R—CO— wherein R is an alkyl group having 8 or more carbon atoms and at least one of the two R groups is an alkyl group having 10 or more, preferably 12–18, carbon atoms, and those of which the two alkyl groups have 12–18 carbon atoms each are preferably used. Such phospholipids include hydrogenated lecithin prepared by hydrogenation of lecithin originated from animals and plants (e.g. egg yolk lecithin, soybean lecithin), and phosphatidyl choline prepared by partial or totally-synthesis which contains mixed acyl groups of lauryl, myristoyl, palmitoyl, stearoyl, etc. Particularly phosphatidyl choline obtained by partial or total synthesis is used advantageously; the concrete examples used preferably are as follows (the observed phase transition temperatures are shown in parentheses): dimyristoylphosphatidyl choline (DMPC, 23.9° C.), palmitoylmyristoylphosphatidyl choline (PMPC, 27.2° C.), myristoylpalmitoylphosphatidyl choline (MPPC, 35.3° C.), dipalmitoylphosphatidyl choline (DPPC, 41.4° C.), stearoylpalmitoylphosphatidyl choline (SPPC, 44.0° C.), palmitoylstearoylphosphatidyl choline (PSPC, 47.4° C.), and distearoylphosphatidyl choline (DSPC, 54.9° C.).

The phase transition temperature of a liposomal membrane is approximate to the phase transition temperature calculated by weight-proportional distribution of those of individual saturated phospholipids used [Reference:

C. G. Knight, "Liposomes; from physical structure to therapeutic applications", Elsevire, North Holland p. 310-311 (1981)], and the composition of saturated phospholipid can be chosen on the basis of this relationship so that the phase transition temperature of the membrane may be fallen in the range described above. By adjustment of the phase transition temperature of the membrane to a temperature in the range described above and by adjustment of the osmotic pressure of the drug-containing solution to be entrapped which is described below, the object of this invention that the liposome compositions show phase transition of the membrane at the temperature of hyperthermia (40°-45° C.) so as to release effectively the drug entrapped can be achieved.

For example, it is advantageous for the object of this invention that the combination of DPPC and DSPC is used at the weight ratio of 95/5 to 70/30, preferably 95/5 to 80/2.

In the present invention, saturated phospholipids are used in an amount of more or 60 weight %, preferably more or 70 weight% in components of the liposomal membrane.

In addition, for formation of the liposomal membrane in the invention, small amounts of various additives, for example antioxidants for stabilization of the membrane, glycolipids such as ganglioside and sulphatide, sodium stearoylmethyl taurate, or octadecanesulfone as charge-controllers, may be used in addition to the saturated phospholipids described above, as far as the phase transition temperature of the membrane is kept in the 40°-45° C. The transition temperature can be adjusted by selection of suitable saturated phospholipids in adequate combination ratios.

The drug-containing solution to be entrapped in liposomes in this invention is preapred so that the osmotic pressure may be 1.2 to 2.5 times higher than that of body fluid of warm-blooded animals. This solution is prepared advantageously by addition of a drug and an osmotic pressure controlling agent to water for adjustment of the osmotic pressure to the 1 level described above. Such an osmotic pressure controlling agent may be any of those which are soluble in water and physiologically acceptable for warm-blooded animals, and used without any particular restriction. For example, salts (e.g. sodium chloride), sugars (e.g. glucose, mannitol, sorbitol), and amino acids (e.g. glycine, aspartic acid, glutamic acid) are used preferably.

In addition, the other substances (e.g. preservatives, stabilizing agents or pH controlling agents) which are employable for preparing a drug composition may be optionally incorporated in said aqueous solution in an appropriate amount provided that the osmotic pressure is kept in the range of 1.2 to 2.5 times higher than that of body fluid of warm-blooded animals.

Especially, a mixture of sodium chloride and a sugar is preferably used as an osmotic pressure controlling agent in order to prepare the liposome composition entrapping cisplatin (CDDP) or its derivatives. In this case, sodium chloride is used in an amount of more than 40 weight parts relative to 1 weight part of the employed CDDP or its derivatives, and a sugar is added so that the osmotic pressure may be 1.2 to 2.5 times higher than that of body fluid of warm-blooded animals. When the osmotic pressure controlling agent described above, the CDDP or its derivatives entrapped in the liposome can be kept more stably during storage.

The drugs used in this invention are those which are expected to show synergistic effects when combined with hyperthermia therapy and which are used for improvement of the targeting effect by entrapment in liposomes. From this standpoint, antitumor agents, are desirable for the drug in this invention. Particularly those which are soluble in water to a certain extent or more, for example, the drug of which logarithm of the partition coefficient in octanol/water is 10 or less are desirable. The examples of such drugs include metal complexes such as cisplatin (CDDP), carboplatin, tetraplatin, and iproplatin, anticancer antibiotics such as adriamycin, mitomycin C (MMC), actinomycin, ansamitocin or the derivatives thereof (e.g. 9-thiomeitancin), bleomycin, Ara-C, daunomycin, metabolic antagonists such as 5-FU, methotrexate, and TAC-788 [isobutyl 5-fluoro-6-(E)-furfurylideneaminoxy-1,2,3,4,5,6-hexahydro-2,4-dioxopyrimidine-5-carboxylate, Japanese Unexamined Patent Application No. 13780/1984], alkylating agents such as BCNU and CCNU, and other antitumor agents such as melpharan and mitoxantrone, as well as lymphokines such as natural and recombinant interferons ($\alpha$, $\beta$, $\gamma$) natural and recombinant interleukin 2. Among these drugs, those which are expected to show synergistic effects when combined with hyperthermia therapy and which improve markedly the targeting effect by entrapment in liposomes, that is, those which show high clearance when given in the form of solutions are used advantageously, because, as Hunt et al. pointed out in relation to the method of administration of a drug, rapid elimination from the body (high clearance) is a requirement for a drug used for improvement of the targeting effect [Pharmaceutical Research, Vol. 3, p.333(1986)]. In this sense, platinum complexes such as CDDP are expected much to show synergistic effect when combined with hyperthermia therapy, and used particularly favorably because they show high clearance.

The amount of a drug to be entrapped in liposomes may be chosen adequately on the basis of the therapeutic dose and the unit dose, though, in general, the conditions of preparation of liposomes are chosen so that the amount to be entrapped may be as large as possible.

The liposome compositions in this invention are prepared by using the components of the membrane and the solution to be entrapped as described above. Liposomes are classified roughly into 3 groups, i.e. multilamellar vesicles, MLV, small unilamellar vesicles, SUV, and large unilamellar vesicles, LUV, which can be prepared by the known methods. In this invention LUV are the most desirable because they can improve more effectively the targeting effect at the temperature of hyperthermia. LUV include also the reverse-phase evaporation vesicles, REV, and oligolamellar vesicles.

The methods for preparation of LUV which are commonly used include (1) the REV method, (2) the dialysis-detergent method, and (3) the French press method, which can be applied in this invention as follows:

Method (1):

To the solution (oil phase) which has been obtained by dissolving a saturated phospholipid in an organic solvent, a solution (water phase) containing one of the drug described above and an osmotic pressure-adjusting agent is added to obtain a W/O emulsion, followed by evaporation of the organic solvent to form a gel, and a liposome preparation of this invention is obtained by further evaporation of the organic solvent. As the organic solvent, diethyl ether, isopropyl ether, or chloroform is used advantageously. These organic solvents may be used in combination; for example, a mixture of one volume of chloroform and 1 to 1.5 volumes of isopropyl ether is used. At least 0.8 volumes of an organic solvent is used per unit volume of the aqueous solution but usually 3 volumes or less of the organic solvent is used because the organic solvent in excess in undersirable. An organic solvent in excess will make it difficult to adjust the osmotic pressure of the drug-containing solution to be entrapped in liposomes as well as to scale up the production of liposome preparations.

Method (2):

A saturated phospholipid is solubilized in water phase containing a drug and an osmotic pressure-controlling agent in the presence of an appropriate detergent, followed by dialysis of the resultant solution to remove the detergent gradually, to give a liposome preparation of this invention [J. Brunner et al., Biochmi. Biophys. Acta, 445, 322 (1976)].

Method (3):

By using a saturated phospholipid and an aqueous solution containing a drug and an osmotic pressure-controlling agent, MLV or SPLV (stable plurilamellar vesicles) are prepared according to a conventional method, followed by filtration under pressure through a filter of a suitable pore size, to give a liposome preparation of this invention [M. J. Hope et al., Biochmi. Biophys. Acta, 812, 55 (1985)].

As a method for preparation of liposomes, the methods for preparation of LUV such as the dehydration-rehydration vesicle method [C. Kirby et al., Biotechnology, Nov., 979 (1984)]may also be used.

Liposome compositions prepared by these methods are used as they are but in general it is desirable that they are dispersed in solutions suitable for the purpose of use after removal of the drug which has not been entrapped in liposomes. Removal of the drug is performed by dialysis of the liposome composition placed in a dialysis bag.

In the dialysis, the not-entrapped drug (free drug) can be removed very efficiently in such a way that the solution containing liposomes which have entrapped the drug and not-entrapped drug is poured into holllow fiber and then a dialyzing fluid is allowed to flow through the hollow fiber. Specifically, for desirable dialysis, the aqueous fluid containing a liposome composition is flowed into hollow fiber (about 25 cm, effective membrane area, 1.5 m$^2$) at the rate of about 150 ml/min., and a dialyzing fluid is allowed to flow at the rate of about 500 ml/min. so that the membrane pressure on hollow fiber may become 0. An appropriate number of hollow fiber bundles arranged in parallel may improve the efficiency of dialysis. By dialysis using hollow fiber the free drug can be removed completely from 500 ml of a solution of a liposome preparation in as short as 25 minutes.

The dialyzing fluid may be physiological saline solution only for removal of a free drug, but a dispersion is favorable which is suitable for administration when the preparation is used for therapeutic purpose by intravenous injection as described later. In the latter case, for example an aqueous solution of the osmotic pressure-controlling agent described above may be used as the dialyzing fluid.

The particle diameter of the liposomes in this invention is adjusted generally to a diameter in the range of 0.1–2 μm, preferably 0.1–0.5 μm. The particle diameter may be adjusted for example by selecting the operation conditions for homogenization of the W/O emulsion during preparation of liposomes according to Method (1) described above, or by selecting the liposomes of a diameter suitable for the purpose of use by filtration of a liposome preparation through a membrane of a suitable pore size.

The liposome compositions in this invention can be used for treatment of tumor according to the nature of the drug to be included. For example, the liposome composition entrapping an antitumor agent is very effective therapeutically when injected intravenously in tumor-bearing warm-blooded animals (e.g. laboratory animals such as rabbit, rat and mouse; pet animals such as dog and cat; and human being) in hyperthermia. In this case the composition is administered after dispersing in a suitable dispersion according to a conventional method, so that the composition may be administered by injection or drip-feed. Such a dispersion may be the aqueous solution of an osmotic pressure-controlling agent described above, and the osmotic pressure is usually isotonic to the body fluid of the warm-blooded animals, though it may be hypertonic up to a pressure two times higher than that of the body fluid.

The dose may be determined appropriately according to the disease, the symptoms, and the nature of the antitumor agent; for example, it is desirable that a liposome composition entrapping CDDP is administered so that the unit dose of CDDP in an adult may be about 0.5–50 mg, preferably about 0.5–30 mg. It is most desirable that administration is begun about 5–15 minutes after the beginning of hyperthermia therapy, though earlier administration is permissible because it does not cause any trouble. Hyperthermia is brought about by any method as far as it is localized and the site of lesion is heated to 40°–45° C. Therefore the liposome compositions in this invention are useful as antitumor compositions for treatment of solid tumors (e.g. intestinal cancer, lung cancer, breast cancer, cancer in urinary organs, cutaneous cancer, cerebral tumor, etc.) which may be treated by hyperthermia therapy.

The liposome compositions in this invention are characterized in that the phase transition temperature of the membrane is in the range of 40°–45° C. and the osmotic pressure of a drug-containing solution to be entrapped in liposomes is 1.2 to 2.5 times hihger than that of body fluid of warm-blooded animals. The liposome compositions in which an antitumor agent has been entrapped release a sufficient amount of the agent at 40°–45° C., and therefore are expected to have evident antitumor effect when combined with hyperthermia therapy.

FIG. 1 shows the antitumor effect observed after administration of the CDDP-entrapping liposome composition in this invention to mice in comparison with that in the control group.

In the following this invention is illustrated more detail with Examples, Experimental Examples and Test Examples.

EXAMPLE 1

540 mg of DPPC and 60 mg of DSPC were dissolved in the 1:1 mixture of chloroform and isopropyl ether in a 0.2 1-beaker. Separately CDDP was dissolved in water, and sodium chloride was dissolved in this solution so that the osmotic pressure might be 1.9 times higher than that of physiological saline, to give an aqueous salt solution containing CDDP at 500 μg/ml. Thirty ml of this solution was added to the solution of a saturated phospholipid described above, and emulsified in an emulsator (Polytron, Kinematika) for 10 minutes and then in a probe-type sonicator (Ohtake Seisakusho, Japan) for further 20 minutes, to give a W/O emulsion. The resultant emulsion was placed in a 0.5 l-eggplant-shaped flask and the organic solvent was evaporated off in a rotary evaporator at 60° C under reduced pressure, to give LUV. The resultant LUV was filtrated through a filter of 1.2 μm in pore size (Acrodisc, Gelman). The osmotic pressure of the solution of the drug to be entrapped in liposomes was confirmed at this time to be 1.9 times higher than that of the body fluid (Note 1). Then the LUV dispersion thus obtained was dialyzed through a dialysis membrane (Spectrapor, Spectrum Medical) against physiological saline for 24 hours to remove the free CDDP contained in the liposome dispersion, to give a liposome composition in which CDDP was entrapped together with the hypertonic solution described above. The proportion of CDDP entrapped in liposomes at this time was 26.5% (Note 2), 0 and the phase transition temperature of the membrane of liposomes was about 41° C.

Note 1. Measurement of osmotic pressure

The osmotic pressure of the drug-containing solution to be entrapped in liposomes, the dispersion in which liposomes are dispersed (dialyzing fluid), or the test solution for the release test of liposomes was measured in an osmometer (Osmometer, Amuco) by using 3 ml each of the solutions. The osmotic pressure of the drug-containing solution entrapped actually in liposomes was assumed to be equal to that of the solution outside the liposomes (the dispersion medium) measured in the osmometer by using 3 ml of the liposome composition before dialysis, obtained by evaporation of the organic solvent. It was confirmed by addition of lipid and by measurement of osmotic pressure after dialysis of the liposome drug against a dialyzing fluid of a known osmotic pressure that liposomes suspending in the solution do not affect the osmotic pressure of the solution outside the liposomes.

Note 2. Quantification of CDDP entrapped in liposomes and the free CDDP remaining in the solution outside the liposomes (dispersion meidum)

The amount of CDDP entrapped in liposomes was determined by atomic absorption analysis (Hitachi, Japan) of platinum in the mixture of 0.1 ml of a mixture, which consists of 0.1 ml of a liposome composition and 1.9 ml of physiological saline, and 24 ml of distilled water. The amount of CDDP suspending in the solution outside the liposomes was determined by atomic absorption analysis of platinum in the 25-fold dilution with distilled water of the filtrate obtained by filtration of about 2 ml of the mixture consisting of 0.1 ml of a liposome composition and 1.9 ml of physiological saline through Centrisart filter (SM 13249 E, Sartrius). The entrapment rate in liposomes was calculated as the ratio of the concentration of the drug entrapped in liposomes to the concentration of the drug used for preparation of the liposome composition.

Note 3. Measurement of phase transition temperature of liposomal membrane

Phase transition temperature of liposomal membrane was determined in DSC (Seiko, Japan) by using 15 μl of a liposome composition in a sampler (rate of heating: 5° C./min.).

EXAMPLE 2

In a similar manner as in Example 1 a CDDP-entrapping liposome composition was obtained, except that the osmotic pressure of the CDDP-containing solution to be entrapped in liposomes was adjusted to be 1.7 times higher than that of physiological saline.

EXAMPLE 3

In a similar manner as in Example 1 a CDDP-entrapping liposome composition was obtained, except that the osmotic pressure of the CDDP-containing solution to be entrapped in liposomes was adjusted to be 1.5 times higher than that of physiological saline.

EXAMPLE 4

In a similar manner as in Example 1 a CDDP-entrapping liposome composition was obtained, except that the osmotic pressure of the CDDP-containing solution to be entrapped in liposomes was adjusted to be 2.1 times higher than that of physiological saline.

EXAMPLE 5

In a similar manner as in Example 1 a CDDP-entrapping liposome composition was obtained, except that the 2:3 mixture of chloroform and isopropyl ether was used in place of the 1:1 mixture of chloroform and isopropyl ether.

EXAMPLE 6

In a similar manner as in Example 2 a CDDP-entrapping liposome composition was obtained, except that 60 ml of the 1:1 mixture of chloroform and isopropyl ether was used in place of 30 ml of the mixture in Example 2.

EXAMPLE 7

In a similar manner as in Example 2 a CDDP-entrapping liposome composition was obtained, except that 24 ml of the 1:1 mixture of chloroform and isopropyl ether was used in place or 30 ml of the mixture in Example 2.

EXAMPLE 8

DPPC (4.5 g) and 0.5 g of DSPC were dissolved in 250 ml ,of the 1:1 mixture of chloroform and isopropyl ether in a 0.5 l-beaker. To this solution was added 250 ml of a solution of CDDP in physiological saline at the concentration of 500 μg/ml which had been prepared beforehand so that the osmotic pressure might be 1.9 times higher than that of physiological saline, which was emulsified in an emulsator (Polytron, Kinematika) for 10 minutes and then in a bath-type sonicator (Laboratory Supplies, New York) for further 20 minutes to give a W/O emulsion. The resultant emulsion was placed into a 1 l-eggplant-shaped flask and treated in a rotary evaporator. Then after evaporation of the organic solvent and dialysis in a similar manner as in Example 1, a liposome composition entrapping CDDP together with the hypertonic solution described above was obtained.

EXAMPLE 9

DPPC (18 g) and 2 g of DSPC were dissolved in 1000 ml of the 1:1 mixture of chloroform and isopropyl ether in a 2 l-beaker. To this solution was added 1000 ml of a solution of CDDP of 500 μg/ml in saline which had been prepared beforehand so that the osmotic pressure might be 1.9 times higher than that of physiological saline, mixed slightly, and emulsified in an emulsator (homomixer for 3 1, Tokushukika, Japan) for 60 minutes, to give a W/O emulsion. The emulsion thus obtained was subjected to evaporation of the organic solvent in the same homomixer at 60° C. under reduced pressure, to give LUV. A portion (500 ml) of the resultant LUV was poured into an apparatus for dialysis (hollow fiber manufactured by Asahi Kasei, Japan: fiber length; about 25 cm, effective membrane ara: 1.5 m², inner diameter; 200 μm, membrane thickness; 20 μm) at the rate of about 150 ml/min. and physiological saline as the dialyzing fluid was allowed to flow at the rate of about 500 ml/min. so that the membrane pressure on the hollow fiber might become 0; thus free CDDP was removed by dialys,is, and a liposome composition entrapping CDDP together with the hypertonic solution described above was obtained.

EXAMPLE 10

Thirty ml of the liposome composition before dialysis obtained in Example 9 was dialyzed against saline which had been prepared so that the osmotic pressure of the saline might be 1.5 times higher than that of physiological saline in a similar manner as in Example 1 for removal of free CDDP, to give a liposome composition.

EXAMPLE 11

Thirty ml of the liposome composition before dialysis obtained in Example 9 was dialyzed against a glucose solution which had been prepared so that the osmotic pressure of the glucose solution might be 1.9 time higher than that of physiological saline in a similar manner as in Example 1 for removal of free CDDP, to give a liposome composition.

EXAMPLE 12

Thirty ml of the liposome composition before dialysis obtained in Example 9 was dialyzed against a salt-glucose solution which had been prepared by addition of glucose to physiological saline so that the osmotic pressure of the glucose solution might be 1.9 times higher than that of physiological saline in a similar manner as in Example 1 for removal of free CDDP, to give a liposome composition.

EXAMPLE 13

In a similar manner as in Example 1 a CDDP-entrapping liposome composition was obtained, except that 480 mg of DPPC and 120 mg of DSPC were used in place of 540 mg of DPPC and 60 mg of DSPC used in Example 1. The phase transition temperature of the liposomal membrane of this preparation was about 41° C.

EXAMPLE 14

In a similar manner as in Example 1 a CDDP-entrappi liposome composition was obtained, except that 600 mg of DPPC and 60 mg of sodium stearoylmethyl taurate (SMT) were used in place of 540 mg of DPPC and 60 mg of DSPC used in Example 1. The phase transition temperature of the liposomal membrane of this preparation was about 41° C.

EXAMPLE 15

In a similar manner as in Example 1 a CDDP-entrapping liposome composition was obtained, except that 600 mg of DPPC and 60 mg of octadecanesulfonic acid (ODS) were used in place of 540 mg of DPPC and 60 mg of DSPC used in Example 1. The phase transition temperature of the liposomal membrane of this preparation was about 42° C.

EXAMPLE 16

In a similar manner as in Example 1 a CDDP-entrapping liposome composition was obtained, except that 540 mg of DPPC and 60 mg of sulphatide (SF) were used in place of 540 mg of DPPC and 60 mg of DSPC used in Example 1. The phase transition temperature of the liposomal membrane of this preparation was about 41° C.

EXAMPLE 17

In a similar manner as in Example 1 a 5-FU-entrapping liposome composition was obtained, except that 200 μg/ml of 5-FU was used in place of 500 μg/ml of CDDP in Example 1.

EXAMPLE 18

In a similar manner as in Example 1 a TAC-788-entrapping liposome composition was obtained, except that 200 μg/ml of TAC-788 was used in place of 500 μg/ml of CDDP in Example 1.

EXAMPLE 19

In a similar manner as in Example 1 a 9-thiomeitancin-entrapping liposome composition was obtained, except that 50 μg/ml of 9-thiomeitancin (Japanese Unexamined Patent Application No. 192381/82) was used in place of 500 μg/ml of CDDP in Example 1.

EXAMPLE 20

In a similar manner as in Example 1 an MMC-entrapping liposome composition was obtained, except that 200 μg/ml of MMC was used in place of 500 μg/ml of CDDP in Example 1.

EXAMPLE 21

In a similar manner as in Example 1 an aclarubicin-entrapping liposome composition was obtained, except that 500 μg/ml of aclarubicin was used in place of 500 μg/ml of CDDP in Example 1.

EXAMPLE 22

In a similar manner as in Example 1 a daunomycin-entrapping liposome composition was obtained, except that 1 mg/ml of daunomycin was used in place of 500 μg/ml of CDDP in Example 1.

EXAMPLE 23

In a similar manner as in Example 1 a BCNU-entrapping liposome composition was obtained, except that 200 μg/ml of BCNU was used in place of 500 μg/ml of CDDP in Example 1.

EXAMPLE 24

In a similar manner as in Example 1 a CCNU-entrapping liposome composition was obtained, except that 200 μg/ml of CCNU was used in place of 500 μg/ml of CDDP in Example 1.

EXAMPLE 25

In a similar manner as in Example 1 an interleukin 2 (IL-2)-entrapping liposome composition was obtained, except that 308 μg/ml of IL-2 was used in place of 500 μg/ml of CDDP in Example 1.

EXAMPLE 26

DPPC (560 mg) and 40 mg of DSPC were dissolved in the 1:1 mixture of chloroform and isopropyl ether in a 0.2 l-beaker. Separately in 30 ml of water were dissolved 10 mg of CDDP, 60 mg of sodium chloride and 1530 mg of mannitol. Thirty ml of this solution was added to the solution of a saturated phospholipid described above, and emulsified in an emulsator (Polytron, Kinematica) for 10 minutes and then in a probe-type sonicator (Ohtake Seisakusho, Japan) for further 20 minutes, to give a W/O emulsion. The resultant emulsion was placed in a 0.5 l eggplant-shaped flask and the organic solvent was evaporated off in a rotary evaporator at 60° C. under reduced pressure, to give LUV. The resultant LUV was filtrated through a filter of 1.2 μm in pore size (Acrodisc, Gelman). The osmotic pressure of the solution of the drug to be entrapped in liposomes was confirmed at this time to be 1.8 times higher than that of physiological saline. The LUV dispersion thus obtained was dialyzed through a dialysis membrane (Spectrapor, Spectrum Medical) against physiological saline for 24 hours to remove the free CDDP contained in the liposome dispersion, to give a liposome composition in which CDDP was entrapped together with the hypertonic solution described above.

EXPERIMENTAL EXAMPLE 1

The liposome compositions obtained in Example 1 to 16 were tested for their release on heating (Note 4) into physiological saline, and the results are shown in Table 1. Namely, all of the liposome compositions obtained in Examples 1 to 16 released little CDDP when heated at 39° C (less than 1%), retaining stably the drug within liposomes unless they were heated to the temperature of hyperthermia. At 42° C. 70% or more CDDP was released, i.e. the preparations are excellent in release on heating because they release most of the drug on heating to the temperature of hyperthermia.

Note 4. Test for release on heating of liposome compositions 0.1 ml of a liposome composition was dispersed in 1.9 ml of physiological saline or saline of which osmotic pressure had been adjusted to a value (the solution for the release test), and the amount of CDDP released into the solution outside the liposomes (the solution for the release test) after heating at 39° C. or 42° C. for 15 minutes was determined by the same method as that described in Note 2 for determination of free CDDP in the solution outside liposomes. The rate of release was expressed by a percentage to the content in the liposome composition.

TABLE 1

| Sample | Osm (in)[a] | rate of release (%) 39° C. | rate of release (%) 42° C. |
| --- | --- | --- | --- |
| Example 1 | 1.9 | 0.0 | 89.5 |
| Example 2 | 1.7 | 0.0 | 79.6 |
| Example 3 | 1.5 | 0.1 | 75.2 |
| Example 4 | 2.1 | 0.2 | 86.9 |
| Example 5 | 1.9 | 0.9 | 89.5 |
| Example 6 | 1.5 | 0.0 | 86.9 |
| Example 7 | 1.9 | 0.1 | 83.2 |
| Example 8 | 1.9 | 0.1 | 84.4 |
| Example 9 | 1.9 | 0.6 | 81.9 |
| Example 10 | 1.9 | 0.3 | 80.7 |
| Example 11 | 1.9 | 0.0 | 80.0 |
| Example 12 | 1.9 | 0.0 | 82.6 |
| Example 13 | 1.9 | 0.0 | 70.8 |
| Example 14 | 1.9 | 0.3 | 74.9 |

TABLE 1-continued

| Sample | Osm (in)[a] | rate of release (%) 39° C. | rate of release (%) 42° C. |
| --- | --- | --- | --- |
| Example 15 | 1.9 | 0.2 | 71.4 |
| Example 16 | 1.9 | 0.0 | 99.3 |

[a]The osmotic pressure of the drug containing solution entrapped in liposomes, expressed in relative values taking the osmotic pressure of physiological saline as 1.

EXPERIMENTAL EXAMPLE 2

Samples of the liposome composition of Example 1 were tested for the release on heating at other temperatures than 39° C. and 42° C.; the rate of release was 0.0% at 37° C., 0.0% at 38° C., 10.3% at 40° C. 88.4% at 41° C., and 76.0% at 45° C. Thus the samples were confirmed to release a sufficient amount of the drug in the range of temperature of hyperthermia but to retain stably the drug within liposomes at lower temperatures. In a separate experiment, a sample of the liposome composition described above was allowed to flow through a thin tube (PE50) at a fixed rate, a part of the tube was heated, and the amount of CDDP released on heating was determined; it was shown that most of the drug was released within a few seconds at the temperature of hyperthermia, and thus the release of the drug from liposomes on heating at the temperature of hyperthermia was confirmed to occur almost explosively and complete in a short time.

EXPERIMENTAL EXAMPLE 3

Liposome compositions were prepared in the same manner as in Example 1 except that the osmotic pressure of the CDDP-containing solution to be entrapped in liposomes was adjusted to 0.6 times, 0.8 times, and 1.0 time higher than that of physiological saline (Samples 1, 2, and 3). Sample 4 was a CDDP-entrapping liposome composition prepared so that the osmotic pressure of the CDDP-containing solution to be entrapped in liposomes might be 3.0 times higher (which is higher than that in the liposome compositions in this invention) and the osmotic pressure of the dialyzing fluid might be 2.5 times higher than that of physiological saline. Separately, a CDDP-entrapping liposome composition (Samples 5 and 6) which showed a phase transition temperature of the membrane higher than that of hyperthermia was prepared in the same manner as in Example 1 except that 300 mg of DPPC and 60 mg of DSPC (phase transition temperature: 48° C.) or 600 mg of DSPC (phase transition temperature: 55° C.) were used in place of 540 mg of DPPC and 60 mg of DSPC used in Example 1. These samples were tested for their release on heating by using physiological saline as the test solution, and the results are shown in Table 2. Namely, as shown by the rate of release at 42° C. of Samples 1, 2, and 3 in Table 2, when the osmotic pressure of the drug-containing solution to be entrapped in liposomes was too low, the drug was not released sufficiently at the temperature of hyperthermia. In addition, as shown by the rate of release at 38° C. of Sample 4, when the osmotic pressure of the drug-containing solution to be entrapped in liposomes was too high, liposomes became unstable and let leak a part of the drug not in heat-dependent manner which is different from the release based on phase transition of the liposomal membrane. As shown by the rate of release at 42° C. of Sample 5 and 6, when the phase transition temperature of the liposomal membrane was higher than the temperature of hyperthermia, the drug was not released on heating even when the osmotic pressure of the drug-containing solution to be entrapped had been adjusted appropriately.

TABLE 2

| Sample | Osm (in)[a] | rate of release (%) 39° C. | rate of release (%) 42° C. |
|---|---|---|---|
| Sample 1 | 0.6 | 0.0 | 0.0 |
| Sample 2 | 0.8 | 0.0 | 2.5 |
| Sample 3 | 1.0 | 0.0 | 30.4 |
| Sample 4 | 3.0 | 38.7 | 95.8 |
| Sample 5 | 0.6 | 0.0 | 0.0 |
| Sample 6 | 0.8 | 0.0 | 0.0 |

[a]The osmotic pressure of the drug-containing solution entrapped in liposomes, expressed in relative values taking the osmotic pressure of physiological saline as 1.

EXPERIMENTAL EXAMPLE 4

The liposome compositions obtained in Examples 1 and 3 were tested for their release on heating when the osmotic pressure of the test solution was varied, and the results are shown in Table 3. Namely, these results indicate that the influence of the osmotic pressure on the rate of release of liposomes may be roughly dependent on the ratio of the osmotic pressure of the drug-containing solution entrapped in liposomes to that of the test solution for the test of release on heating (Osm(in)/Osm(out) in Table 3). This indicates that, to attain the excellent release (more than about 70%) at 42° C. as shown in Experimental Example 1 under a different osmotic pressure of the test solution, the osmotic pressure of the drug-containing solution entrapped in liposomes is required to be 1.2 times higher than that (about 300 Osm) of the body fluid into which liposomes should actually release the drug on heating, and less than 2.5 times for sufficient stability of liposomes (they do not release at a temperature lower than 38° C.).

TABLE 3

| Sample | Osm (in)[a] | Osm (out)[b] | Osm (in)/ Osm (out) | rate of release (%) 39° C. | rate of release (%) 42° C. |
|---|---|---|---|---|---|
| Example 1 | 1.9 | 0.6 | 3.16 | 47.7 | 73.8 |
|  | 1.9 | 0.8 | 2.42 | 2.4 | 87.5 |
|  | 1.9 | 1.0 | 1.90 | 1.6 | 89.5 |
|  | 1.9 | 1.2 | 1.58 | 1.2 | 68.6 |
|  | 1.9 | 2.4 | 0.79 | 0.1 | 21.0 |
| Example 3 | 1.5 | 0.6 | 2.50 | 48.8 | 84.4 |
|  | 1.5 | 0.8 | 1.87 | 0.3 | 86.9 |
|  | 1.5 | 1.0 | 1.50 | 0.1 | 79.6 |
|  | 1.2 | 1.2 | 1.20 | 0.0 | 53.7 |
|  | 1.5 | 1.5 | 1.00 | 0.3 | 33.9 |

[a]The osmotic pressure of the drug-containing solution entrapped in liposomes, expressed in relative values taking the osmotic pressure of physiological saline as 1.
[b]The osmotic pressure of the test solution for test of release on heating, expressed in relative values taking the osmotic pressure of physiological saline as 1.

EXPERIMENTAL EXAMPLE 5

The amount of CDDP leaked from liposomes after the liposome compositions obtained in Examples 1 and 8 were kept in a cold place (about 5° C.) for 3 months was 2% or less in each case. Thus the liposome compositions in this invention were shown to be very stable.

TEST EXAMPLE

Meth A tumor-bearing mice (BALB/C, female mice, 5 mice per group, mean body weight: 20 g) were given intravenously dilutions in physiological saline of the CDDP-entrapping liposome composition obtained in Example 1 at the dose of 10, 20, and 40 μg of CDDP per mouse. During the period from 15 minutes till 30 minutes after the beginning of injection only the site of tumor (under the skin at the flank) was heated to 40 to 45° C. with a hot plate. Twenty-one day after two once-a-day injections, the weight of the tumor was measured. The ratio (T/C) of the mean tumor weight in the group treated with the liposome preparation (T) to that in the untreated group (C) was calculated, and the results are shown in FIG. 1. In the Figure, —●— shows the values for the group given the liposome preparation in this invention with heating, —○— for the group given only CDDP without heating, —●— for the group given the liposome composition in this invention without heating, and o for the group given an aqueous solution of CDDP with heating.

As seen from this Figure, administration of the liposome composition in this invention with heating brought about evident antitumor effect.

What we claim is:

1. A liposome composition for hyperthermia therapy comprising:
   (1) liposomes entrapping a first aqueous solution containing an antitumor agent and an osmotic pressure controlling agent, said liposomes having a membrane which has a main component of phospholipids whose acyl groups are saturated acyl groups, said membrane having a phase-transition temperature of 40°–45° C., and said first aqueous solution having an osmotic pressure of 1.2 to 2.5 times higher than that of body fluid of warm-blooded animals, and
   (2) a second aqueous solution having an osmotic pressure in a ratio of about 0.8 to 1 relative to that of the body fluid of the warm-blooded animals into which said liposomes are dispersed,
   wherein the composition is injectable.

2. The composition according to claim 1, wherein the phospholipids are a mixture of dipalmitoylphosphatidyl choline and distearoylphosphatidyl choline, and wherein the ratio of dipalmitoylphosphatidyl choline and distearoylphosphatidyl choline is 95/5 to 70/30 by weight.

3. The composition according to claim 1, wherein the phase transition temperature is 40° to 43° C.

4. The composition according to claim 1, wherein the antitumor agent is cisplatin.

5. The composition according to claim 1, wherein the osmotic pressure controlling agent is a physiologically acceptable salt, a sugar or an amino acid, or a mixture of them.

6. The composition according to claim 1, wherein the liposomes are large unilamellar vesicles.

7. The composition according to claim 1, wherein the drug is cisplatin, the osmotic pressure controlling agent is a mixture of sodium chloride and mannitol, and the liposomes are large unilamellar vesicles whose membranes are constituted from dipalmitoylphosphatidyl choline and distearoylphosphatidyl choline so that the phase transition temperature is 40° to 43° C.

8. The composition according to claim 1, wherein the drug is cisplatin, wherein the osmotic pressure controlling agent is a physiologically acceptable salt or a sugar, or a mixture thereof, wherein the phospholipids are a mixture of dipalmitoylphosphatidyl choline and distearoylphosphatidyl choline, and wherein the ratio of dipalmitoylphosphatidyl choline and distearoylphosphatidyl choline is 95/5 to 70/30, wherein the liposomes are large unilamellar vesicles, wherein the phase transition temperature of the membrane is 40° to 43° C., and wherein the liposomes are dispersed in physiological saline.

9. A method for the treatment of solid tumors in hyperthermia therapy, which comprises administering to a subject in need of said treatment a therapeutically effective amount of the composition according to claim 1.

10. A method for producing a liposome composition for hyperthermia therapy, which comprises the steps of:
  (1) preparing a first aqueous solution containing an antitumor agent and an osmotic pressure controlling agent, said first aqueous solution having an osmotic pressure which is adjusted to 1.2 to 2.5 times higher than that of body fluid of warm-blooded animals,
  (2) mixing said first aqueous solution with a solution which is prepared by dissolving one or more members of phospholipids in an organic solvent to form a W/O emulsion, wherein said phospholipids have acyl groups which are saturated acyl groups and are capable of forming a liposome having a membrane with a phase-transition temperature of 40° to 45° C., and wherein said organic solvent is used in 0.8 to 3 volumes per unit volume of said first aqueous solution,
  (3) evaporating the organic solvent to prepare liposome vesicles entrapping the antitumor agent, wherein said liposome vesicles have a membrane with a phase-transition temperature of 40° to 45° C., and
  (4) dispersing the thus obtained liposomes in a second aqueous solution having an osmotic pressure in a ratio of about 0.8 to 1 relative to that of the body fluid of the warm-blooded animals, wherein the composition is injectable...

11. The method according to claim 10, wherein the organic solvent is one or more member selected from the group consisting of diethyl ether, isopropyl ether and chloroform.

12. The method according to claim 10, wherein the organic solvent is a mixture of one volume of chloroform and 1 to 1.5 volumes of isopropyl ether.

13. The method according to claim 10, wherein the phospholipids are a mixture of dipalmitoylphosphatidyl choline and distearoylphosphatidyl choline, and wherein the ratio of dipalmitoylphosphatidyl choline and distearoylphosphatidyl choline is 95/5 to 70/30 by weight.

14. The method according to claim 10 wherein the phase transition temperature of the membrane is 40° to 43° C.

15. The method according to claim 10, wherein the antitumor agent is cisplatin.

16. The method according to claim 10, wherein the osmotic pressure controlling agent is a physiologically acceptable salt, a sugar or an amino acid or a mixture thereof.

17. The method according to claim 10, wherein the liposomes are large unilamellar vesicles.

18. The method according to claim 10, wherein the drug cisplatin, wherein the osmotic pressure controlling agent is a mixture of sodium chloride and mannitol, and wherein the liposomes are large unilamellar vesicles whose membranes are constituted from dipalmitoylphosphatidyl choline and distearoylphosphatidyl choline so that the phase transition temperature is 40° to 43° C.

* * * * *